US00PP20936P2

(12) United States Plant Patent
Carruth

(10) Patent No.: US PP20,936 P2
(45) Date of Patent: Apr. 20, 2010

(54) GRANDIFLORA ROSE PLANT NAMED 'WEKGOBNEZ'

(50) Latin Name: *Rosa hybrida*
Varietal Denomination: WEKgobnez

(75) Inventor: Thomas F. Carruth, Altadena, CA (US)

(73) Assignee: Weeks Wholesale Rose Grower, Inc., Pomona, CA (US)

( * ) Notice: Subject to any disclaimer, the term of this patent is extended or adjusted under 35 U.S.C. 154(b) by 74 days.

(21) Appl. No.: 12/290,414

(22) Filed: Oct. 30, 2008

(51) Int. Cl.
*A01H 5/00* (2006.01)

(52) U.S. Cl. ..... Plt./132
(58) Field of Classification Search ..... Plt./132
See application file for complete search history.

(56) References Cited

U.S. PATENT DOCUMENTS

PP8,279 P 6/1993 McGredy, IV
PP10,334 P 4/1998 Carruth

*Primary Examiner*—Annette H Para
(74) *Attorney, Agent, or Firm*—McKee, Voorhees & Sease, P.L.C.

(57) ABSTRACT

A new variety of Grandiflora rose suitable for garden decoration, having flowers of burgundy and cream striped bicolor coloration.

1 Drawing Sheet

Classification: The present invention relates to a new *Rosa hybrida* plant.

Variety denomination: The new plant has the varietal denomination 'WEKgobnez'.

BACKGROUND OF THE INVENTION

This invention relates to a new and distinct variety of Grandiflora Rose. It has as its seed parent the variety known as 'WEKcalroc' (U.S. Plant Pat. No. PO10,334) and as its pollen parent the variety known as 'MACgenev' (U.S. Plant Pat. No. 008,279).

SUMMARY OF THE INVENTION

Among the features which distinguish the new variety from other presently available and commercial rose cultivars known to the inventor are the following combinations of characteristics: its strong damask to citrus-like fragrance, its unique flowers of burgundy & cream striped bicolor coloration and its many stipitate glands on the sepal margins. The plant has an upright moderately spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKgobnez' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'WEKcalroc' by the following combination of characteristics: whereas 'WEKgobnez' bears very double flowers (about 41 to 66 petals) of burgundy & cream striped bicolor coloration, 'WEKcalroc' bears double flowers of striped red and yellow coloration with significantly lesser petalage (about 29 to 35 petals). The new variety is classified as a grandiflora rose with an upright moderately spreading medium height growing habit (about 140 to about 165 cm. in height), whereas the seed parent is classified as a floribunda rose with a significantly shorter bushy compact upright low to medium height growing habit (about 90 to about 130 cm. in height).

The new variety may be distinguished from its pollen parent, 'MACgenev' by the following combination of characteristics: whereas 'WEKgobnez' bears very double flowers (about 41 to 66 petals) of burgundy & cream striped bicolor coloration, 'MACgenev' bears double flowers of light pink coloration with significantly lesser petalage (about 25 to 30 petals). The new variety bears average size flowers (about 7.7 to about 9.6 cm. in diameter), whereas the pollen parent bears significantly larger flowers (about 18.0 cm. in diameter).

COMPARISON WITH THE CLOSEST COMMERCIALLY AVAILABLE CULTIVAR

The new variety may be distinguished from its closest commercially available cultivar, 'WEKplapep' by the following combination of characteristics: whereas 'WEKgobnez' bears very double flowers (about 41 to 66 petals) of burgundy & cream striped bicolor coloration, 'WEKplapep' bears double flowers of striped red and white coloration with significantly lesser petalage (about 31 to 36 petals). The new variety is classified as a grandiflora rose with an upright moderately spreading growing habit (about 140 to about 165 cm. in height), whereas the closest commercially available cultivar is classified as a floribunda rose with a significantly shorter bushy upright to rounded growing habit (about 90 to about 120 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of October. Phenotypic expression may vary with environmental, cultural and climatic conditions, as well as differences in conditions of light and soil.

BOTANICAL DESIGNATION

The new variety botanical designation is *Rosa hybrida* 'WEKgobnez'.

FLOWER

The new variety usually bears its flowers singly, sometimes in clusters of two to three per stem. Flowers may be borne in regular rounded clusters on strong medium length stems (about 25 to about 68 cm.). Outdoors, the plant blooms abundantly and nearly continuously during the growing season. The flowers have a strong damask to citrus-like fragrance.

BUD

The peduncle is about 2.9 to about 6.6 cm. in length, of average caliper (about 0.2 to about 0.3 cm. in diameter), and usually erect. It is moderately smooth, with some stipitate glands and few hairs. Peduncle color is between 146B and 139B often moderately suffused, especially on the side exposed to the sun, with between 183B and 187B.

Before the calyx breaks, the bud is about 1.2 to about 1.5 cm. in diameter at the widest point, about 1.4 to about 1.9 cm. in length, and moderately globular to somewhat ovoid in shape. The surface of the bud bears few foliaceous appendages and stipitate glands, usually with slender entire foliaceous parts extending beyond the tip of the bud about ½ or more of its length. Bud color is between 146A and 139B sometimes lightly suffused, especially on the side exposed to the sun, with between 183B and 187B.

The sepals are about 2.2 to about 3.3 cm. in length and about 0.5 to about 0.8 cm. in width at the widest point. The outer surface color of the sepal is between 146A and 139B sometimes lightly suffused, especially on the side exposed to the sun, with between 183B and 187B. The inner surface color of the sepal is near 138B broadly bordered by near 137A. The inner surface of the sepal is covered with fine wooly tomentum; sepal margins are lined with many stipitate glands and hairs.

The receptacle of the flower is of short length (about 0.2 to about 0.4 cm.) and moderately thin in caliper (about 0.6 to about 0.8 cm. in diameter). The receptacle is moderately urn-shaped to somewhat flat in form. Its surface is very smooth with some hairs and with somewhat thin fleshy walls. The receptacle color is between 146B and 139B.

As the petals open (after the calyx breaks), the bud is about 1.7 to about 2.0 cm. in diameter at the widest point, about 1.8 to about 2.3 cm. in length, and moderately globular to somewhat ovoid in form. The color of the under surfaces of the newly opened petals is between 12D and 13D sometimes moderately blushed with between 60B and 59C to as dark as between 187B and 187A. At the point where the petal attaches, there is a moderately large zone of between 1C and 154C. The color of the upper surfaces of the newly opened petals is irregularly striped and flecked with as dark as between 187A and 53A to as light as between 11C and 13D sometimes lightly suffused on the lighter color with near 60D. At the point where the petal attaches, there is a moderately large zone of between 4B and 3C.

BLOOM

When fully open, the bloom ranges from about 7.7 to about 9.6 cm. in diameter. Petalage is very double with about 41 to 66 petals and about 3 to 11 petaloids irregularly arranged. When partially open, the bloom form is moderately globular to cupped, and the petals are loosely spiraled to cupped with petal edges somewhat reflexed outward. When fully open, the bloom form is more cupped, and the petals are loosely cupped with petal edges moderately reflexed outward.

PETALS

The substance of the petals is moderately heavy and of somewhat thin thickness, with upper surfaces moderately satiny to somewhat velvety and under surfaces shiny. The petals are about 2.8 to about 5.3 cm. in length and about 1.8 to about 5.6 cm. in width at the widest point. Petal margins are entire.

The outer petals are moderately obovate in shape with rounded apices.

The inner petals are moderately oblanceolate to somewhat obovate in shape with rounded apices.

Petaloids are about 1.1 to about 3.3 cm. in length and about 0.7 to about 2.3 cm. in width at the widest point. Petaloids are irregularly shaped moderately oblanceolate to somewhat subulate with rounded apices.

NEWLY OPENED FLOWER

The under surface color of the outer, intermediate and inner petals is between 4D and 155B sometimes moderately blushed with between 60B and 61C. There is no visible change in coloration at the point where the petal attaches. The upper surface color of the outer, intermediate and inner petals is irregularly striped and flecked with as dark as between 53A and 46B to as light as between 4D and 155B sometimes lightly suffused on the lighter color with between 57C and 61C. At the point where the petal attaches, there is a moderately large zone of between 3D and 2C.

The under and upper surface color of the petaloids are similar in coloration to the upper and under surfaces of the intermediate and inner petals.

The general tonality of the newly opened flower is irregularly striped and flecked with as dark as between 53A and 46B to as light as between 4D and 155B sometimes lightly suffused on the lighter color with between 57C and 61C.

THREE-DAY-OLD FLOWER

The under surface color of the outer, intermediate and inner petals is between 4D and 155B sometimes moderately blushed with between 61B and 61C. There is no visible change in coloration at the point where the petal attaches. The upper surface color of the outer, intermediate and inner petals is irregularly striped and flecked with as dark as between 60A and 46B to as light as between 4D and 155B sometimes moderately suffused on the lighter color with between 57C and 6C. At the point where the petal attaches, there is a moderately large zone of near 2D.

The under and upper surface color of the petaloids are similar in coloration to the upper and under surfaces of the intermediate and inner petals.

The general tonality of the three-day-old flower is irregularly striped and flecked with as dark as between 60A and 46B to as light as between 4D and 155B sometimes moderately suffused on the lighter color with between 57C and 61C.

On the spent bloom, the petals usually drop off cleanly.

In October in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 150) and are arranged regularly about the pistils; a few are mixed with petaloids. The filaments are of medium length (about 0.4 to about 0.7 cm.) most with anthers. Filaments are between 2B and 3B in color. The anthers are somewhat large for the class and all open approximately at the same time. Anther color when immature is near 22B on the external part and near 11D on the internal part. Anther color at maturity is near 165B on the external part and near 200B on the internal part. Pollen is abundant and between 18B and 19C in color.

FEMALE REPRODUCTIVE ORGANS

Pistils vary in number (average about 110). The styles are moderately even, somewhat long in length (about 0.6 to about 0.9 cm.), moderately thin in caliper, and loosely separated to somewhat columnar. Stigma color is between 6C and 8A. Style color is between 1C and 154C sometimes moderately blushed near the top with between 53B and 53C. Ovaries are usually all enclosed in the calyx.

Hips are of somewhat long length (about 1.4 to about 2.3 cm.), moderately globular to somewhat rounded in form, and between 33B and 34B in color when ripe. The hip surface is very smooth with thick fleshy walls. The sepals are moderately fugacious and usually straight in shape.

The seeds are irregularly rounded, smooth in texture, approximately 8 to about 15 per hip, about 0.3 to about 0.5 cm. in diameter at the widest point and between 161B and 162C in color.

FOLIAGE

The compound leaves are usually comprised of three to seven leaflets and are borne abundantly. The five-leaflet leaves are about 7.9 to about 12.9 cm. in length and about 6.7 to about 10.1 cm. in width at the widest point, moderately heavy to somewhat crisp in texture, and glossy in finish on the upper side and matte in finish in the under side. The terminal leaflets are about 4.4 to about 6.3 cm. in length and about 2.8 to about 4.5 cm. in width at the widest point, shaped moderately ovate to somewhat oval with acute apices and rounded bases. Their margins are usually simply serrate.

The upper surface color of the mature leaf is between 139A and 139B. The under surface color of the mature leaf is between 147B and 139C. The upper surface color of the young leaf is between 147A and 137A, usually heavily suffused with between 187A and 183A. The under surface color of the young leaf is between 139B and 138A, usually heavily suffused with between 187B and 183B.

The rachis is of average size caliper and rough. The upper side is deeply grooved with few hairs and some stipitate glands on the edges of the grooves. The under side of the rachis is rough with few stipitate glands and small prickles. The rachis color is near 146C on the under side and near 146A on the upper side. The rachis is often heavily suffused on the young leaves with between 187A and 183A.

The stipules are about 0.8 to about 1.4 cm. in length and of medium width (about 0.5 to about 0.7 cm.) with long straight points that usually turn out at an angle of more than 45 degrees and sometimes recurve toward the stem. The stipule color is between 137B and 146A sometimes heavily suffused especially on the young leaves with between 187A and 183A.

The petiole is of average size caliper and rough. The upper side is deeply grooved with few hairs and some stipitate glands on the edges of the grooves. The under side of the petiole is rough with few stipitate glands and small prickles. The petiole is about 0.9 to about 1.4 cm. in length and about 0.1 to about 0.15 cm in diameter at the widest point. The petiole color is near 146C on the under side and near 146A on the upper side. The petiole is often heavily suffused on the young leaves with between 187A and 183A.

The plant displays an above average degree of resistance to powdery mildew and rust as compared to other commercial varieties grown under comparable conditions in Pomona, Calif. The plant's winter hardiness and drought/heat tolerance are yet to be determined.

GROWTH

The plant has an upright moderately spreading medium height growing habit (about 140 to about 165 cm. in height and about 50 to about 58 cm. spread at the widest point), with full branching. It displays vigorous growth and the canes are of medium size caliper for the class (about 0.9 to about 1.8 cm. in width at the widest point).

The color of the major stems is between 147B and 146A. They bear several large prickles that are about 1.1 to about 1.4 cm. in length. The large prickles are almost straight to angled slightly downward with a somewhat short broad oval base; prickle color is near 165A. The major stem bears many small prickles of similar shape and coloration.

The color of the branches is between 146A and 139B. They bear many large prickles which are of similar size and shape to the large prickles on the major stems; prickle color is between 165B and 164A. The branches bear some small prickles of similar shape and coloration.

The color of the new shoots is between 146B and 139B often moderately suffused with between 187B and 183B. They bear many large prickles which are of similar size and shape to the large prickles on the major stems; prickle color is near 152B often moderately suffused with between 187C and 183C. The shoots bear some small prickles of similar shape and coloration.

I claim:

1. A new and distinct Grandiflora rose plant of the variety substantially as described and illustrated herein.

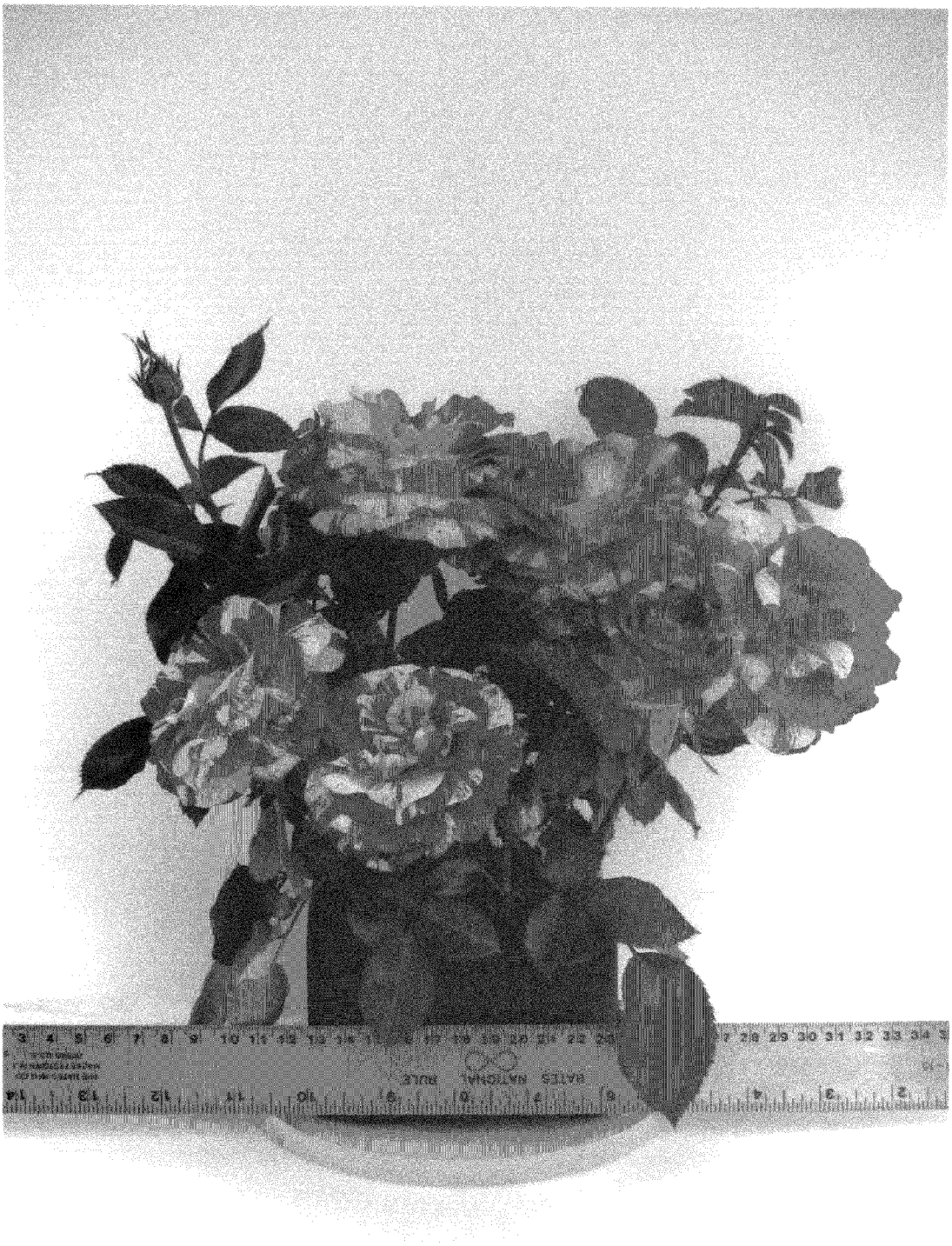

* * * * *